United States Patent [19]

Tomb et al.

[11] 4,025,667

[45] * May 24, 1977

[54] ENZYME CARRIERS

[75] Inventors: William H. Tomb, Corning; Howard H. Weetall, Elmira, both of N.Y.

[73] Assignee: Corning Glass Works, Corning, N.Y.

[ * ] Notice: The portion of the term of this patent subsequent to Jan. 1, 1991, has been disclaimed.

[22] Filed: July 30, 1973

[21] Appl. No.: 383,890

Related U.S. Application Data

[62] Division of Ser. No. 227,205, Feb. 17, 1972, Pat. No. 3,783,101.

[52] U.S. Cl. .............................. 427/215; 427/226; 428/406
[51] Int. Cl.² ........................................... B05D 7/00
[58] Field of Search ............ 117/100 S, 105, 107.2, 117/123 B, 124 B; 427/215, 226; 428/404, 405, 406; 252/454; 260/429.3; 264/DIG. 49; 55/522, 523, 524

[56] References Cited

UNITED STATES PATENTS

| | | | |
|---|---|---|---|
| 2,831,780 | 4/1958 | Deyrup | 65/60 |
| 3,232,782 | 2/1966 | Shannon | 117/100 S |
| 3,403,015 | 9/1968 | Grubb et al. | 117/124 B |
| 3,519,467 | 7/1970 | Plumat et al. | 117/123 B |
| 3,519,538 | 7/1970 | Messini et al. | 195/68 |
| 3,522,075 | 7/1970 | Kiel | 427/226 |
| 3,658,568 | 4/1972 | Donley | 264/60 |
| 3,669,841 | 6/1972 | Millet | 195/63 |
| 3,691,089 | 9/1972 | Janzon | 117/100 S |
| 3,709,833 | 1/1973 | Thomas | 252/454 |
| 3,743,491 | 7/1973 | Poole et al. | 117/124 B |
| 3,783,101 | 1/1974 | Tomb et al. | 195/63 |

*Primary Examiner*—Michael R. Losignan
*Assistant Examiner*—S. Silverberg
*Attorney, Agent, or Firm*—James A. Giblin; Clinton S. Janes, Jr.; Clarence R. Patty, Jr.

[57] ABSTRACT

The half-life of enzymes which have been immobilized by chemical coupling via silane coupling agents to inorganic carriers is increased significantly by using a carrier which has been treated to increase its water-durability. Treatment of the carrier comprises the steps of first coating the carrier with a solution containing a metal, the oxide of which is more water-durable than the carrier, and then firing the coated carrier to form a continuous metal oxide layer on the carrier surface. The treated carriers are then silanized for chemical coupling wih enzymes. Methods for preparing and using enzyme composites having the improved carrier are disclosed.

1 Claim, 2 Drawing Figures

ENZYME CARRIERS

This is a division of application Ser. No. 227,205, filed Feb. 17, 1972, now U.S. Pat. No. 3,783,101.

BACKGROUND OF THE INVENTION

Field of the Invention

In recent years, there has been a growing recognition that enzymes can be used effectively in analytical, medical, and industrial applications. Enzymes are biological catalysts and all known enzymes are proteins having a relatively high molecular weight. As catalysts, enzymes can promote various chemical reactions which utilize specific enzymes or enzyme systems. Typically, an enzyme system acts on one or more compounds designated substrates to produce one or more products.

Enzymes have been classified into various groups depending on the reactions they promote and the substrates they can act upon. These groups of enzymes (e.g., hydrolytic enzymes, redox enzymes, transferase enzymes) are known in the art and they can be conveniently broken down into sub-groups which are commonly descriptive of the substrate the enzyme can act upon (e.g., redox enzymes are those that catalyze oxidation or reduction reactions and which include, for example, the enzyme glucose oxidase which promotes the oxidation of glucose).

Enzymes are normally soluble in an aqueous solution. This solubility has made it difficult to readily remove the enzymes from a solution for repeated use and/or to maintain the catalytic activity of the enzymes for extended periods of time. For those reasons, and because of the growing use of enzymes, various methods have been developed to insolubilize or immobilize the normally soluble enzymes in such manners that the enzymes retain their activity, can be readily removed from a reaction solution, and used repeatedly.

Enzymes have been insolubilized and immobilized in a variety of ways. For example, enzyme composites have been made by physyically entrapping enzymes in such organic materials as starch gel, polyacrylamide gel, agar and the like. They have also been insolubilized by chemically coupling them via azo linkage to cellulose derivatives and to polyaminostyrene beads. Enzymes have also been insolubilized on polytyrosyl polypeptides and in colloidion matrices.

Several disadvantages have been associated with using the above organic materials. The organic materials have been found subject to microbial attack resulting from the presence of carbon atoms in the polymer chain whereby the carrier is broken down and the enzymes become solubilized. Also, many organic carriers have poor heat stability and thus, are difficult to sterilize by such means as an autoclave. Further, some organic materials lack dimensional stability when used in columns and an increase or decrease in swelling of the materials can affect the flow rates of a substrate flowing through the column or the conformation of an attached enzyme. The above disadvantages, and others, associated with using organic carriers or organic matrices for insolubilizing or immobilizing enzymes led to the development of enzyme composites utilizing inorganic carriers. The present invention represents an improvement in the field of enzyme composites which utilize inorganic carriers.

Prior Art

In U.S. Pat. No. 3,556,945, assigned to the assignee of the present invention, there are disclosed enzyme composites in which the enzyme is adsorbed to an essentially insoluble inorganic carrier such as porous glass. In U.S. Pat. No. 3,519,538, also assigned to the same assignee, there are disclosed enzyme composites which consist of inorganic carriers to which enzymes are chemically coupled via intermediate silane coupling agents. In the above patent, it is pointed out that by chemically coupling the enzymes to an inorgaic carrier, the problems associated with organic carriers are avoided as well as the limitations associated with adsorbing enzymes to inorganic carriers, e.g., adsorption of enzymes to inorganic carriers results in a relatively weak bond (compared to covalent coupling) and it is not general for all enzymes since a loss of activity results when there is adsorptive bonding at the active sites on the enzyme molecule. The present invention is an improvement of the inventions disclosed in the above enzyme coupling patent and the teachings of that patent are incorporated herein by reference to that patent (U.S. Pat. No. 3,519,538).

In the above patent it was disclosed that chemically coupled enzymes retained their activity for considerably greater time periods than the corresponding soluble, noncoupled enzyme. However, even though the chemically coupled enzyme composites were found to retain their activity much longer than the free, soluble enzymes, there have been certain disadvantages associated with the coupled enzyme composites. The main disadvantage relates to the half-life of the composites. The term half-life, as used herein, refers to the period of time which elapses before the composite loses one-half of its original enzymatic activity. Enzymatic activity is commonly measured in activity units. Each unit refers to an amount of product which can be produced through the catalytic action of an enzyme over a given time period at a given temperature and pH. For example, the activity of the enzyme glucose isomerase (which converts glucose to fructose), when expressed in terms of International Units (IU), can be expressed as follows:

One unit (IU) = the production (or capability of production) of 1 $\mu$ mole fructose per minute at 60° C., pH 6.85. Also, the activity of the enzyme glucoamylase (which converts starch to dextrose) is commonly expressed in terms of International Units (although not accepted officially) such that one unit = the production (or capability of production) of 1 $\mu$ mole dextrose per minute at 60° C., pH 4.5. An enzyme system can be assigned an operational half-life, based on activity loss with time or a calculated half-life based on initial and final activity.

Even though chemically coupled enzymes have demonstrated half-lives longer than free enzymes, such half-lives have generally been measurable in hours, days, or weeks rather than months or years. This relatively limited half-life of coupled enzymes has greatly limited their utility. This is especially true in industry, since it has been found in some cases that the cost of preparing and using chemically coupled enzyme composites of limited half-life may not generally result in significant cost savings over conventional usage of the free, soluble enzyme.

If an immobilized enzyme composite is to compete economically with the corresponding soluble enzyme, its cost of manufacture and usage must be at least as low as the cost and usage of the soluble enzymes needed to produce a given amount of product. The value of an insolubilized enzyme composite is generally related directly to its half-life and the amount of enzyme which can be loaded on a given amount of carrier. Thus, if an enzyme composite has a half-life such that the cost of its manufacture and use to produce a given amount of product is less than the cost of using the free enzyme to produce the same amount of product, then the value of the enzyme composite becomes greater than the value of the free enzyme. Accordingly, it then becomes more feasible to use the insoluble enzyme composite. For this reason, considerable attention has been directed toward discovering methods for increasing the half-life of enzyme composites having inorganic carriers.

We have now discovered methods for preparing an insolubilized enzyme composite which has a significantly longer half-life than previously obtained. Our discovery was quite surprising since we found the half-life of insoluble enzyme composites having an inorganic carrier is not as much attributable to the nature of the enzyme itself or the enzyme coupling procedure as it is to the inorganic carriers used in the coupled enzyme composite.

SUMMARY OF THE INVENTION

We have discovered methods of preparing immobilized enzyme composites having a calculated half-life of up to 645 days. This significant increase in half-life is thought to be attributable to an improved inorganic carrier which is more durable in an aqueous environment than past inorganic carriers. The new carrier is prepared by coating a less water-durable base carrier with a more water-durable metal oxide which comprises a continuous metal oxide layer on the surface of the base carrier. The preferred coating treatment comprises the steps of coating the base carrier with a solution containing a metal, the oxide of which is more water-durable than the base carrier, and then firing the coated carrier at between 200° C. and 800° C. for about 1 to 4 hours, depending on the metal oxide to be formed, thereby forming a continuous metal oxide surface layer on the base carrier. As the term is used herein, base inorganic carrier refers to any inorganic carrier which is less water-durable than a metal oxide (s) which can be used to coat it.

When porous glass is used as a base carrier, a preferred final coat consists of a thin, continuous surface layer of zirconium oxide. Such a surface metal oxide layer can be formed by first coating the base carrier with a solution containing zirconium in either an organic or aqueous solution, and then firing the coated base carrier to leave a thin, continuous surface layer of zirconium oxide. Tis surface layer may be silanized and modified for chemical coupling to enzymes by known means.

SPECIFIC EMBODIMENTS

The base carriers that may be used in employing the principles of the present invention are any of the carriers disclosed in U.S. Pat. No. 3,519,538 since the present invention represents an improvement over those carriers and composites. Preferably, the base carriers are porous materials (e.g., porous glass) so that a large surface area per unit weight and volume of carrier is available. The base carriers are thinly coated with a treating agent which enhances the durability of the carrier in an aqueous environment. Having increased durability, the coated carriers will have less solubility in water. This lower solubility is thought to be responsible for the increase in half-life of enzyme composites utilizing the coated inorganic carriers. With less dissolution of the carrier, there is less release of the coupled enzyme into a solution. With less release of the enzyme, there is an overall increase in the half-life of the composite since the enzyme is less likely to deactivate when maintained in an immobilized or insolubilized state.

The improved carriers are prepared by forming a thin, continuous layer of at least one metal oxide on the surface of the base carrier so that the durability of the coated carrier in an aqueous environment is better than the durability of the base carrier. By limiting the more durable coating to the surface of the base carrier, small amounts of relatively expensive coating agents can be used to coat a relatively less expensive base carrier which comprises the bulk of the overall weight of the treated carrier. For example, when the base carrier is porous glass, any metal oxide coating (or a mixture of metal oxide coatings) which will form a thin, continuous layer on the surface can be used as long as it provides an overall increase in durability. Also, a durable metal oxide coating on an extremely porous base carrier having a high surface area yields a product having both high surface area and greater durability. Thus, in those cases where a durable metal oxide cannot be prepared in a form having a high surface area, a coating of the same oxide on a base material having such a surface area provides a carrier having both desired properties. Among the metal oxides which can be used to coat a base carrier such as porous glass (mainly amorphous silica) are the oxides of such metals as zirconium, titanium, aluminum, hafnium, and like metals, the oxides of which are more water-durable than porous glass. It is thought that metal oxide coatings or combinations of coatings for base carriers other than porous glass can be readily determined and prepared by one skilled in the art since the solubilities of various base carrier materials can be found in appropriate handbooks. Once the solubility of the base carrier is known, a more water-durable metal oxide, or mixture of oxides, can be chosen as the coating material. Such coating material can be applied by known methods such as by applying or contacting a solution of the metal to the base carrier and then firing the treated carrier to leave the oxide of the metal. Alternatively, the coatings may be applied by the illustrative detailed methods described below.

To apply the coating oxides in a thin, continuous layer, the metal may be applied as a metallo-organic compound such as, for exampl, a salt in an organic solution, an inorganic ester, or a chelate of the metal, which, after application, is convertible by further treatment to the metal oxide. The conversion of the metallo-organic compound to the respective metal oxide may be accomplished by heating the coated carrier to burn off the organic material, thus leaving a metal oxide coating which will enhance the durability of the base carrier.

Zirconium oxide may also be applied to the base carrier by using an aqueous solution. For example, zirconyl chloride or nitrate may be used as a starting material to coat the base carrier by dissolving about 30g $ZrOCl_2$ or zirconyl nitrate in 250 ml. $H_2O$ for each 100g of porous glass. This solution is mixed with the porous base carrier which is then placed under a vacuum for about 15 minutes to remove air from the pores and allow the solution to enter the pores. The treated porous carrier is then dried overnight at an elevated temperature (e.g., 145° C.) and then fired at about 375° C. for 3 hours. This treatment results in a coated carrier having a $ZrO_2$ coating comprising about 8% by weight of the coated carrier. Other methods for applying metal oxide coatings are discussed below.

In a preferred embodiment, the coated carrier of the present invention comprises a porous, granular, inorganic material which has a thin, continuous, surface layer of zirconia or titania. To prepare such carriers, a porous inorganic base material (e.g., porous glass particles or beads, 40 to 80 mesh, 500A average por diameter) is first dried to free it of surface water that is not chemically combined in the base carrier.

A solution of a chelated metal such as zirconium or titanium in an organic solvent is prepared (typically containing the equivalent of 8% oxide). This solution may be prepared by diluting DuPont Tyzor AA with methanol if a coating consisting essentially of a titania oxide is desired, or the solution may be made by dissolving in methanol equimolar quantities of zirconium acetonate and tetrapropopyl zirconate if a coating consisting essentially of a zirconium oxide is desired. The dry base carrier is then saturated with the solution at room temperature and then carefully dried at or above the boiling point of the organic solvent. Preferably, contact with moisture is avoided and the sample is dried with dry air.

After drying, the impregnated material is placed in a furance and heated to a temperture of about 200° C. to 800° C., depending on the coating solution and the base carrier, and held thereat for about 1 to 4 hours. Preferably, the temperature is raised by about only 50° C. per hour. While still warm, the material is removed from the furnace and stored in sealed jars until ready for silanization and enzyme coupling. At this point, the treated carrier consists of the base carrier having a thin, continuous coating of essentially the metal oxide or oxides chosen to coat the base carrier.

The oxide groups, being on the surface, are available for bonding to the silicon portion of a silane coupling agent in accordance with the teachings of U.S. Pat. No. 3,519,538. Accordingly, any of the silane coupling agents disclosed therein may be coupled to the treated carriers with the result that the silanized treated carriers can be generally represented as Base carrier-MeO-Silane where Me represents the metal, the oxide of which forms the thin continuous layer over the base carrier.

By following the teachings of U.S. Pat. No. 3,519,538, the organo-functional portion of the silane coupling agent may be appropriately modified for the chemical coupling of the enzyme which is to be insolubilized or immobilized. For example, the organo-functional groups of the silane may be modified for diazotization and then diazotized for azo coupling to the enzyme if an azo-type coupling will not generally interfere with the enzymes active sites. Also, glutaraldehyde may be used to modify the silane for enzyme coupling. As pointed out in the above patent, the preferred silane-to-enzyme bond will depend on the active sites sought to be protected in a particular enzyme. Thus, the modification of the organo-functional portion of the silane should be based on the directions given in the above patent from which appropriate silane coupling agents may be chosen. Once the enzyme is coupled via the intermediate silane coupling agent to the coated base carrier, it can be represented by the following general formula:

Base carrier-MeO-Silane-Enzyme where Me represents the metal of the metal oxide coating of the base carrier, or a mixture of metal oxides, having an overall greater durability than the base carrier. The silane portion of the silane coupling agent is attached to the coated carrier, the metal oxide layer being disposed between the base carrier and the silane coupling agent. The organic portion of the coupling agent is coupled to the enzyme.

The Control Enzyme Composites

For half-life comparison purposes the enzymes glucoamylase and glucose isomerase were chemically coupled via intermediate silane coupling agents to untreated (uncoated) porous glass samples by known methods. The preparation of the control composites involved the steps of drying the uncoated carrier, silanizing it, and then coupling the enzyme to the silane by either azo linkage or glutaraldehyde reaction. The steps for silanization and azo linkage can be found in U.S. Pat. No. 3,519,538. The glutaraldehyde reaction is essentially described in Habeeb, A.F.S.A., Arch. Biochem. Biophys., Vol. 119, p. 264 (1967). In the glutaraldehyde reaction, the glutaraldehyde activates the silanized carrier for enzyme coupling. Prior to enzyme coupling, however, the glutaraldehyde-activated silanized carrier is washed exhaustively to remove traces of free glutaraldehyde which are desirably avoided to assure enzyme attachment by chemical coupling rather than cross-linking (glutaraldehyde is a known cross-linking agent for some enzymes).

All control composites used a porous glass carrier of the same average pore size and mesh size as that used as base carriers for the coated base carriers of the present invention. The silanization and enzyme coupling of the control composites were similar to those respective procedures used in preparing the coated enzyme composites. These similar procedures are discussed in detail below under the heading "The Treated Carrier Enzyme Composites." Generally, the only physical difference between the control composites and the compared treated carrier composites was the metal oxide coating developed on the surface of the treated carriers prior to silanization. The base carrier used below was porous glass, commonly referred to as Controlled Pore Glass or simply CPG. Such porous glass may be produced in accordance with the teachings of U.S. Pat. No. 2,106,744 issued to Hood et al., U.S. Pat. No. 3,485,687 issued to Chapman, and U.S. Pat. No. 3,549,524 issued to Haller.

The Treated Carrier Enzyme Composites

Detailed directions for preparing some preferred composites of the present invention are given below. The enzymes glucoamylase and glucose isomerase were chemically coupled to the treated carriers by means of azo linkage or glutaraldehyde reaction in essentially the same manner as for the control composites. Preparation of the composites preferably involve a six-step procedure, as shown in the illustrative steps A–F below.

A. Drying of CPG 20 gram portions (dry basis) of CPG glass (40–80 mesh, pore volume 1.5 ml. per gram) are placed in a covered 350 ml. evaporating dish and removed to a circulating air oven operating at 200° C. After 2 hours, the samples are removed and placed in a desiccator. The desiccator is pumped to a pressure of 1½ inches of Hg or less and this pressure maintained until the sample ceases "boiling." The vacuum is then broken with dry nitrogen. The sample is then returned to the drying oven for another 2 hours or more and then again placed in the desiccator and the pressure reduced by means of a pump to 1½ inches of Hg or less.

If boiling occurs a second time, pumping is continued until it ceases, the vacuum broken with dry nitrogen, and the sample is again returned to the drying oven for 2 hours or more. If no boiling occurs, the desiccator is washed once with air, and the vacuum broken with dry nitrogen and the sample is allowed to cool to room temperature. The sample is weighed when it is removed from the desiccator and it is then ready for impregnation with the coating solutions. The drying steps above are merely illustrative and other techniques may be used depending on the material dried and equipment available.

B. Preparation of Coating Solutions

As noted above, a wide variety of metal oxides may be used as a coating for the base carrier since the only requirement for the metal oxide(s) surface layer is that it is more durable in an aqueous environment than the base carrier. Thus, various forms of a given metal or combination of metals such as salts, chelates, inorganic esters, and the like may be used in either an aqueous or organic solution to coat the base carrier. This coating may then be converted to a surface metal oxide layer by heat treatment or other techniques which will leave a metal oxide surface. It is thought that other methods of applying a metal oxide surface layer to an inorganic body could be used to prepare the coated carriers. For example, it is well known that metals can be applied to surfaces by vapor deposition, sputtering, or similar techniques. Such metal deposits can then be converted to metal oxides by a variety of means such as, for example, by heat treatment. In the specific examples below, however, the coating was applied as a metal chelate solution which, after firing, left a metal oxide surface layer of zirconium oxide. The detailed methods for preparing zirconium chelate coating solutions are merely illustrative. Two alternative methods for preparing such a solution are given. The coating solution of the first method was the one used in the subsequent steps which resulted in the enzyme composites having coated carriers.

1. 8% Chelate Solution No. 40

15.8 grams of zirconium acetylacetonate are dissolved in 69 grams of methanol. To this are added 15.2 grams of 75% tetra-n-propyl zirconate in n-propanol. While considerable heat evolves, the solution stays below boiling and is used immediately because of the tendency for a precipitate to separate slowly. The precipitate is believed to be tetramethyl zirconate.

2. 8% Chelate Solution No. 66

13 grams of 2.4 pentanedione are dissolved in 56.6 grams of benzene and to this with stirring are added 30.4 grams of 75% tetra-n-propyl zirconate. While boiling should not result, the heat of reaction is higher than for No. 40 chelate solution and the reaction should be carried out in an unstoppered flask. This solution is stable and after cooling can be stored in a stoppered bottle for a week at least.

C. Impregnation of the Dried CPG

Approximately 65 grams of the 8% chelate (of method 1, above) was weighed into a small beaker, and added from the beaker with stirring to a 20g portion of dried CPG. The samples was saturated without flooding.

The sample was covered an dried for about at least 6 hours in a circulating oven at 80° C. Violent bumping may occur if the oven temperature is about 90° C. or higher.

D. Firing of the Impregnated and Dried CPG

The impregnated and dried sample was placed in an evaporating dish in a furnace (equipped with a circulating fan) at 80° C. The temperature was raised at the rate of about 50° C. per hour to about 500° C. and that temperature was held for 1 hour to assure oxide formation and then the temperature was allowed to return at furnace rate. When the temperature had dropped to below 300° C., the sample was removed from the furnace and placed in a desiccator and the pressure reduced to 1½ inches of Hg or less. The vacuum was then broken with dry nitrogen. When the sample reached room temperature, it was weighed, places in a glass jar, covered with water, and sealed. It should be noted that the firing temperature and time will depend on the coating used. For the zirconia coating, a temperature of about 500° C. for about 1 hour is preferred although temperatures between about 200° C. and 800° C. for 1 or more hours may be used, depending on the coating, e.g., when the aqueous zirconia solution is used, a temperature as low as about 200° C. for about 1 hour is effective. However, temperatures above 800° C. tend to result in poor coatings.

E. Silanization (e.g., for about 2 g. quantities of carrier)

The desired quantity of zirconia coated CPG is weighed and placed in a large beaker. Ten milliliters of 10% (by volume) aqueous silane, γ-aminopropyltriethoxysilane (A-1100 - Union Carbide), is added to the coated glass and the pH of the mixture immediately adjusted to between 1.0–4.0, the optimum being around 3.5, using 6N HCl. The reaction is carried out at a temperature between 25°–80° C. for 1 to 4 hours, preferably 70° C. for 3.5 hours, with occasional manual stirring. After the completion of the reaction, the glass is washed with distilled water, dried at 100°–125° C. and stored for use.

F. Coupling Enzyme to Silanized Coated Carrier (two procedures)

1. Coupling via Glutaraldehyde Reaction

Ten ml. of 2.5% by weight glutaraldehyde solution (in 0.1M $Na_2HPO_4$ buffer solution at pH 7.0) is added per gram of silanized glass. The pH of the mixture is adjusted to 7.0 ± 0.2 with dilute HCl or NaOH. The reaction mixture is placed in a vacuum desiccator to remove trapped air bubbles and allowed to react at room temperature (25° C.) for 2 to 3 hours. At the completion of the reaction the excess glutaraldehyde is removed by rinsing several times with distilled water. After five or more rinses the excess water is filtered through filter paper (e.g. Whatman No. 41). The glass should immediately be subjected to the final enzyme coupling reaction.

Enzyme solution, dissolved in a minimum amount of water, containing 100 mg. protein per gram of total carrier, is added to the above coated, silanized porous glass. For glucoamylase enzyme, the protein solution is prepared in 0.1M $Na_2HPO_4$ buffer at pH 7.0, while glucose isomerase enzyme solution is prepared in 0.05% $NaHCO_3$ buffer at pH 7.25. Any other enzyme can be coupled at pH 7.0–8.0. Specific directions for coupling other enzymes may be found in U.S. Pat. No. 3,519,538. The reaction is carried out at 5° C. for 3 hours at a pH of 7.0 and 7.25, for glucoamylase and glucose isomerase, respectively. The pH adjustments are made with either dilute NaOH or HCl. After the completion of the coupling reaction, the glass is filtered and washed several times with distilled water. The immobilized enzyme is then stored under refrigeration in an appropriate buffer.

2. Coupling via Diazotization Procedure both glucoamylase and glucose isomerase may be coupled via azo linkage to the silanized coated carrier. The diazotization procedure is preferably carried out at 0° C. in an ice bath. To 1g of silanized, coated, porous glass add 10 ml. of 2N HCl. Next add 0.25g solid $NaNO_2$. Place the entire reaction mixture in a desiccator and attach it to an aspirator to remove air and gas bubbles in the particles. Continue diazotization in aspirator for about 20 minutes. The desiccator is preferably packed in ice.

The product is then removed filtered on a Beucher funnel and washed with ice cold water containing 1% sulfamic acid. Place the diazotized glass in the enzyme solution, using as little liquid as possible (slurry), e.g., the enzyme (100 mg/g of carrier) is dissolved in a minimum amount of water. Previously adjust the enzyme solution to pH 8.0–9.0 and maintain the pH by addition of NaOH. Using a buffer at 0.05M such as $NaHCO_3$ or TRIS may aid in pH control. The reaction is continued for at least 60 minutes. Samples of enzyme may be withdrawn at intervals for protein determination to determine when maximum coupling rate has decreased (usually within 60 minutes). Continued reaction only adds additional enzyme (15–20%), but not necessarily additional activity. Wash the product with distilled water and store in closed container as taken from filter (usually 50–70% water by weight).

In preparing the enzyme composites it is preferred that a magnetic stirrer not be used since it tends to grind the carrier. It is also desirable that the enzyme composites should not be frozen to avoid any cracking of the carrier. Lastly, the final product is preferably not air-dried since that tends to inactivate the enzyme.

Half-Life Comparison Experiments

In the following experiments, the half-lives of composites consisting of the enzymes glucoamylase or glucose isomerase, each chemically coupled to untreated porous glass carriers (control composites), were compared with the half-lives of composites of the same enzymes chemically coupled to the carriers prepared according to the principles of the present invention. The glucoamylase used was obtained from Novo Industries (Denmark). The glucose isomerase used was obtained from the United States Department of Agriculture, North Regional Laboratory, Peoria, Illinois.

The enzyme glucoamylase (amyloglucosidase) catalyzes the conversion of a starch solution to glucose (dextrose). The enzyme glucose isomerase catalyzes the conversion of a glucose solution to fructose. It was thought that these enzyme systems would provide reliable half-life data which would confirm the importance of treating inorganic carriers to achieve greater aqueous durability.

Two major reactor systems were used in the experiments These reactor systems are of the type (but on a smaller scale) that could be expected to be used in industrial applications. In the first reactor system (plug flow), separate columns (15 mm ID) were filled with equal weights (e.g., 8–10g) of the control enzyme composites and the coated carrier enzyme composites. In the case of half-life studies with the glucoamylase, a 30% substrate solution of enzyme-thinned ($\alpha$-amylase) cornstarch was passed through each of the filled columns at predetermined flow rates. Flow rates were adjusted to maintain the hydrolysis at 90% to 93% where possible. In some cases the flow rate was adjusted to set hydrolysis initially at 90% and held constant, while percent hydrolysis was allowed to decay.

For the half-life comparisons with the glucose isomerase, a 50% substrate solution of glucose was passed through the columns containing the glucose isomerase composites, and the flow rates were held constant for all experiments.

The second reactor system was a Continuous Stirred Tank Reactor (CSTR) similar to that disclosed in U.S. Ser. No. 152,507, filed June 14, 1971, and assigned to the same assignee as the present invention. The CSTR design eliminates, among other problems, the problem of pressure drop across a column. The substrate flows into the reactor and out at the same rate as in columns. The CSTR was used only for the half-life comparisons of the glucoamylase experiments, and hydrolysis rates were maintained at close to 90% as possible. Equal weight-control samples and treated carrier samples were used in this reactor. The reactor systems used for the experiments below are identified as such in the tables.

The assay procedures for both the glucoamylase and glucose isomerase comparisons were performed by known means. All activity measurements (E) were made in terms of International Units (IU). One IU of glucoamylase, as commonly used, is defined as the production of 1 $\mu$ mole of dextrose per minute at 60° C., pH 4.5. One IU of glucose isomerase is commonly defined as the production of 1 $\mu$ mole of fructose per minute at 60° C., pH 6.85.

The experiments were designed to determine the "usability" of the immobilized enzyme being compared with the same enzyme which was coupled to untreated carriers. In all experiments, a known amount of the immobilized enzyme (e.g., 8–10g) was placed in the indicated reactors and the respective substrate solutions were passed through the reactors at flow rates necessary to give about 90% starch conversion for the glucoamylase and up to 50% conversion of glucose to fructose for the glucose isomerase. The experiments were continued until the flow rates necessary to maintain the catalysis at the indicated levels precluded continuation of the experiments or until enough time had passed to insure reasonable data. The enzyme derivatives wer assayed, then used in the columns or CSTR, reassayed, and the following parameters were calculated or recorded.

Temperature (°C.) — Experiments were run at 60° C., 45° C., and 37° C. in order to determine the effect of temperature on the remaining parameters.

where $t$ is the time in hours.

Half-Life — The half-life was determined by using the decay constant and determining that point at which 50% of the activity is lost. Although $k$ is given in hours, $t_{1/2}$ is reported in days. For the glucoamylase:

$$t_{1/2} \text{ (days)} = \frac{0.693}{k \text{ (hrs.)}} / 24$$

Results with Uncoated Carriers for Glucoamylase (Controls)

The reactors operated at 60° C. (shown in Table I) showed the greatest degree of variation for all parameters studied. However, there still appeared to be a significant increase in half-life when compared with past work with soluble enzyme systems.

TABLE I

| | Immobilized Glucoamylase on Uncoated Controlled Pore Glass (CPG) | | | | | | | |
|---|---|---|---|---|---|---|---|---|
| System | $E_o$ (Units) | Temp. (° C.) | Volume (ml) | Time (Hrs.) | Decay Constant (Hrs.)$^{-1}$ | Efficiency*** (%) | $t_{1/2}$ (Days) | Reactor No. |
| CSTR-Azo* | 9,042 | 60 | 5,200 | 360 | $6.92 \times 10^{-3}$ | 10 | 4.2 | 4 |
| CSTR-Glut.** | 57,471 | 60 | 16,815 | 528 | $3.35 \times 10^{-3}$ | 21 | 8.5 | 5 |
| CSTR-Glut. | 46,590 | 60 | 12,375 | 504 | $6.34 \times 10^{-3}$ | 33 | 4.5 | 8 |
| CSTR-Azo | 19,157 | 45 | 5,190 | 351 | $1.27 \times 10^{-3}$ | 22 | 22.6 | 3 |
| CSTR-Glut. | 29,880 | 45 | 12,500 | 336 | $2.12 \times 10^{-3}$ | 23 | 13.7 | 7 |

*Represents azo-linkage
**Represents glutaraldehyde coupled
***Efficiency is based on the maximum dextrose production theoretically possible for the enzyme activity available, assuming Michaelis-Menten kinetics.
CSTR represents the reactor used (Continuous Stirred Tank Reactor)
Column indicates columns were used

TABLE II

| | Immobilized Glucoamylase on Uncoated Controlled Pore Glass | | | | | | | |
|---|---|---|---|---|---|---|---|---|
| System | $E_o$ (Units) | Temp. (° C.) | Volume (ml) | Time (Hrs.) | Decay Constant (Hrs.)$^{-1}$ | Efficiency*** (%) | $t_{1/2}$ (Days) | Reactor No. |
| COLUMN-Glut. | 20,843 | 45 | 17,175 | 500 | $1.24 \times 10^{-3}$ | 9.9 | 22.3 | 17 |
| COLUMN-Glut. | 22,682 | 45 | 18,470 | 522 | $1.38 \times 10^{-3}$ | 10.0 | 22.2 | 18 |
| CSTR-Azo* | 12,579 | 37 | 5,500 | 408 | $1.13 \times 10^{-3}$ | 14.0 | 33 | 11 |
| CSTR-Glut.** | 19,770 | 37 | 3,900 | 408 | $0.85 \times 10^{-3}$ | 20 | 44 | 12 |

*Represents azo-linkage
**Represents glutaraldehyde coupled
***Efficiency is based on the maximum dextrose production theoretically possible for the enzyme activity available, assuming Michaelis-Menten kinetics.
CSTR represents the reactor used (Continuous Stirred Tank Reactor)
Columns indicates columns were used Time (hours) — The times the experiments were run were recorded in hours.

Volume — The volume of 30% starch or 50% glucose solutions passed through the reactor during the Time in hours.

Dextrose or Fructose Produced (g.) — The total dextrose or fructose produced was determined by collecting the reactor effluent daily, determining the sugar present in that effluent and totalling the daily accumulations.

Initial Enzyme Activity (E.) — The initial activity was determined in International Units (IU) as defined above for glucoamylase and glucose isomerase.

Final Enzyme Activity (E) — At the end of the experiment the activity of the composites was determined, and the loss of activity was recorded.

Decay Constant ($k$) — The decay constant was calculated by assuming activity loss was exponential, i.e., first order decay was assumed. Thus, $$k = (2.303/t) \log (E_o/E)$$

The present invention is based on the discovery that the carrier must be made more durable in an aqueous environment if greater half-lives are to be achieved. This conclusion was based partially on the following three discoveries: (A) samples of the porous glass carriers in all the 60° C. experiments (Table I) showed increases in pore volume ranging from 4% in one experiment to 29% in another; (B) enzymatic activity could be detected in the dextrose product obtained from the reactors 5 and 7 after storing the solution for several days at 4° C. As can be seen in Table III, the amount of dextrose in the stored solutions increased with time, thus indicating the presence of free enzyme; (C) silicon was found in the reactor effluents in the total silane utilized on the carrier. Samples taken from a system (Reactor No. 11) operated at the lowest temperature (37° C.) and another (Reactor No. 23) were submitted for Si analysis. The results, shown in Table IV, were positive for silicon, reported as silica. The total Si recovered is equivalent to 2.5% of the total carrier weight and could not have come from the silane which equals less than 0.3% Si by weight.

TABLE III

Change in Dextrose Concentration On Storage of Product

| Reactor No. | Days After Collection | Initial Sugar (mg/ml) | Final Sugar (mg/ml) | Change % |
|---|---|---|---|---|
| 5 | 12 | 212 | 272 | 28 |
|   | 18 | 197 | 206 | 5 |
|   | 21 | 209 | 214 | 2 |
| 7 | 6 | 224 | 291 | 30 |
|   | 12 | 284 | 291 | 2 |
|   | 15 | 283 | 278 | −2 |
|   | 19 | 259 | 266 | 3 |
|   | 22 | 231 | 272 | 18 |

Control Collections - No change in sugar concentration on storage.

TABLE IV

Effluent Analysis for Silica

| Reactor No. | Days of Operation | Si as $SiO_2$* (mg/5 ml) |
|---|---|---|
| 11 | 2 | 0.17 |
|    | 10 | 0.11 |
| 23 | 2 | 0.02 |
|    | 3 | 0.03 |
| 33 | 4 | 0 |
|    | 10 | 0 |
| 34 | 4 | 0 |
|    | 10 | 0 |
|    | 15 | 0 |
|    | 20 | 0 |

Attempts were made to increase productivity and decrease dissolution of the untreated carrier by operating at 45° C. and 37° C. These results are given in Tables I and II. However, only slight increases in productivity are observed.

Results with the Improved (Coated) Carriers

Glucoamylase Composites

Figure 1:
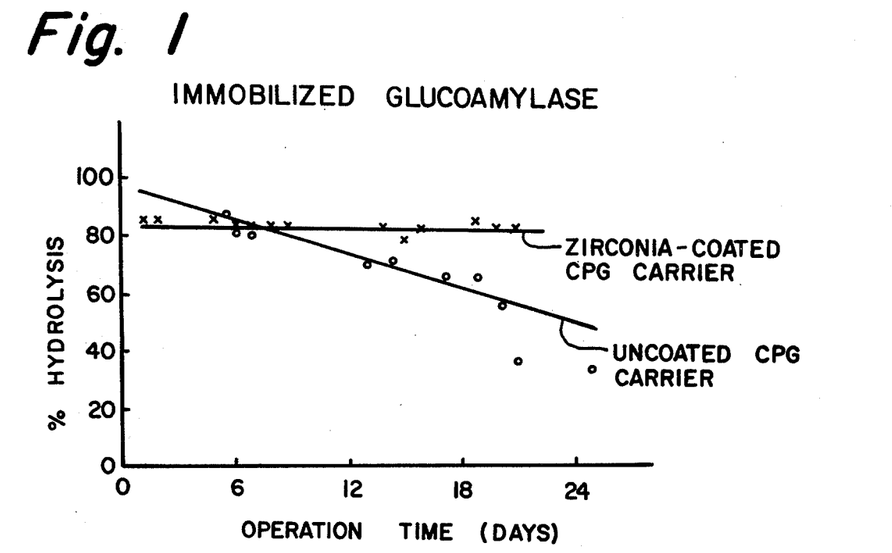
FIG. 1 compares the percent hydrolysis of starch to glucose va. time for glucomylase composites of the present invention and known glucoamylase composites.

The enzyme composites having carriers which were treated according to the teachings of the present invention were studied under similar conditions of catalysis. The porous glass carriers which had been coated with $ZrO_2$ coatings, and then silanized, and coupled with glycoamylase by azo linkages, were used in starch conversion studies, the results of which are summarized and compared with control composites in Table V. From Table V, it can be seen that the coatings of $ZrO_2$ on carriers used in glucoamylase composites resulted in data from which calculated half-lives of 645 days were achieved. These significant improvements in the half-lives of immobilized enzyme composites now makes possible the economical use of enzymes coupled to inorganic carriers since the increase half-life, in turn, greatly increases the value of an immobilized enzyme over free enzymes. Glycoamylase was also coupled to alumina by known means and the resulting composites were used in similar studies which indicated a half-life of 70 days for the alumina-silane-enzyme composite (see Table V). The relatively high half-life found for the alumina carriers confirms the importance of having a carrier of low water solubility since it is known that alumina is less soluble than porous glass. FIG. 1 illustrates the comparative behavior of a composite having an uncoated carrier (carrier experiment 3, Table V), and a zirconium-coated carrier (carrier experiment 5, Table V). Both columns were operated at 45° C.

TABLE V

Comparison of Immobilized Glucoamylase on Controlled Pore Glass and Other Carriers

| Carrier Experiment | $E_o$ (Units) | Temp. (° C.) | Volume (ml) | Time (Hrs.) | Decay Constant (Hrs.)$^{-1}$ | Efficiency (%) | $t_{1/2}$ (Days) | % Loss | Reactor No. |
|---|---|---|---|---|---|---|---|---|---|
| 1-CPG* | 57,471 | 60 | 16,815 | 528 | $3.35 \times 10^{-3}$ | 4.7 | 8.5 | 91 | 5 |
| 2-CPG | 49,042 | 60 | 12,375 | 504 | $6.3 \times 10^{-3}$ | 1.0 | 5 | 96 | 8 |
| 3-CPG | 19,923 | 45 | 10,150 | 552 | $1.33 \times 10^{-3}$ | 18.5 | 21.2 | 53 | 23 |
| 4-CPG-Zr** | 16,245 | 45 | 76,000 | 504 | $4.5 \times 10^{-5}$ | 51 | (645) | 5 | 33 |
| 5-CPG-Zr | 16,245 | 45 | 76,000 | 504 | $4.5 \times 10^{-5}$ | 51 | (645) | 5 | 34 |
| 6-Alumina*** | 4,170 | 45 | 2,400 | 336 | $4.1 \times 10^{-4}$ | 25 | 70 | 16 | 13a |

*CPG represents porous 96% silica glass (controlled pore glass)
**CPG-Zr represents controlled pore glass-Zr coated
***Neutral alumina 200 mesh
Numbers in parenthesis are calculated values based on indicated hours of operation and initial and final activity.

Glucose Isomerase Composites

Comparative experiments with glucose isomerase were performed in essentially the same manner as the glucoamylase tests. In all glucose isomerase studies, however, all conversions of glucose to fructose were carried out in columns (15 mm ID). The substrate, as noted above, consisted of a 50% glucose solution. The runs for both the untreated carrier-enzyme composites and the treated carrier-enzyme composites were in a buffer system of 0.005M $MgSO_4$, 0.001M $CaCl_2$, and 0.02M Maleic Acid, pH 6.85. The temperature for all glucose isomerase conversions was 60° C., and in each experiment, the flow rate was held constant.

Figure 2:
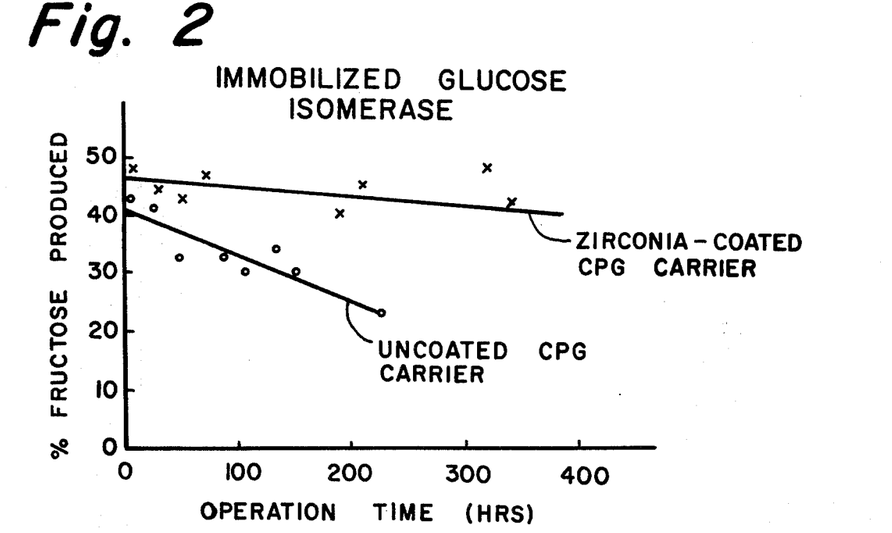
FIG. 2 compares the percent fructose produced from glucose vs. time for glucose isomerase composites of the present invention and known glucose isomerase composites.

FIG. 2 illustrates the results obtained when the untreated carrier coupled to the enzyme glucose isomerase is compared with the composite having a $ZrO_2$-coated carrier prepared according to the above directions. The data of both FIGS. 1 and 2 were fit to a straight line by least squaring the data shown. For both of the composites compared in FIG. 2 the glucose isomerase was chemically coupled to the respective carriers by means of azo linkage. FIG. 2 indicates the significantly greater composite stability achieved in fructose conversion when the inorganic carrier is treated with a coating which is more durable in an aqueous medium than porous glass. As can be seen, by using immobilized glucose isomerase having a $ZrO_2$-coated carrier coupled to it, it is possible to stay closer to a 50% fructose production level for a greater period of operation time. Based on the limited duration of operation of the systems illustrated in FIG. 2, it can be calculated that the half-life of the uncoated carrier composite is about 19 days whereas the calculated half-life for the $ZrO_2$-coated carrier composite is about 75 days. As in the case of the glucoamylase comparison studies, the calculated increase in half-life represents a significant increase in the value of the enzyme composite consisting of an enzyme chemically coupled to an inorganic carrier.

As noted above, the composites of the present invention represent a significant improvement over those composites disclosed in U.S. Pat. No. 3,519,538. The present coated carriers can utilize a base carrier having a very high surface area. Such a large surface area may not be possible with particles of the metal oxide used to coat the base carrier. Thus, although particles of the metal oxides could be used to couple enzymes, thus providing water durable composites, such composites may not have the desired high surface area found in less durable base carriers such as porous glass. Without a high surface area (such as the 5 to 500M$^2$ per gram for porous glass), the amount of enzyme which could be loaded on an uncoated inorganic carrier would be considerably reduced, thus reducing the value of the enzyme composite in much the same way that aa reduced half-life reduces the value of the enzyme composite. Accordingly, the present invention is partially based on the discovery that a more durable metal oxide (which alone may not have the desired porosity and/or surface area) may be used to coat a less durable base carrier (which does have a desired porosity and/or surface area) so that the resulting carrier is water durable and has a large surface area. These carriers then can be used to prepare more durable enzyme composites holding a greater amount of enzyme.

It is thought that the preparation of the coated carriers is subject to numerous variations, all of which can be determined by one skilled in the art. The optimum time-temperature heat treatment for forming metal oxides other than zirconia on base carriers other than porous glass can be readily determined once a particular metal oxide, or mixture of oxides, is chosen as a coating material for a given base carrier. Generally, the heat treatments should be for at least one hour to assure oxide formation. Longer treatments are generally limited by economic considerations or, perhaps, the use of temperatures approaching the higher limit for a given base carrier or coating.

Since the present invention relates primarily to the carrier used in forming an immobilized enzyme composite, and the composite found thereby, it is intended that the above examples should not be limited to the enzyme systems reactor syses, or particular coated carriers used to illustrate the invention.

We claim:
1. A method of improving the water-durability of controlled pore porous glass particles which comprises the steps of:
    a. contacting porous glass particles having a particle size of 40 to 80 mesh with a solution of a chelated zirconium compound; and
    b. heating the particles to a temperature between about 200° C. and 800° C. to form a thin, continuous layer of an oxide of zirconium on the surfaces of the porous glass particles.

* * * * *

UNITED STATES PATENT OFFICE
CERTIFICATE OF CORRECTION

Patent No. 4,025,667         Dated May 24, 1977

Inventor(s) William H. Tomb and Howard H. Weetall

It is certified that error appears in the above-identified patent and that said Letters Patent are hereby corrected as shown below:

Column 3, line 56, "Tis" should be -- This --.

Column 3, line 62, "va." should be -- vs. --.

Column 4, line 64, "exampl" should be -- example --.

Column 7, line 26, "boiling" should be -- "boiling" --.

Column 7, line 29, "boiling" should be -- "boiling" --.

Column 8, line 27, "an" should be -- and --.

Column 8, line 44, "places" should be -- placed --.

Column 9, line 38, "both" should be -- Both --.

Column 11, line 13, "wer" should be -- were --.

Column 11, line 57, "(E.)" should be -- $(E_o)$ --.

Column 11, line 68, "(E./E)" should be -- $(E_o/E)$ --.

UNITED STATES PATENT OFFICE
CERTIFICATE OF CORRECTION

Patent No. 4,025,667  Dated May 24, 1977

Inventor(s) William H. Tomb and Howard H. Weetall

It is certified that error appears in the above-identified patent and that said Letters Patent are hereby corrected as shown below:

Columns 11 and 12, Table II, Column Heading "System", "CSTR-Azo*" should be -- CSTR-Azo --.

Columns 11 and 12, Table II, Column Heading "System", "CSTR-Glut.**" should be -- CSTR-Glut. --.

Column 16, line 12, "syses," should be -- systems, --.

Signed and Sealed this

First Day of November 1977

[SEAL]

Attest:

RUTH C. MASON  
Attesting Officer

LUTRELLE F. PARKER  
Acting Commissioner of Patents and Trademarks